US009827102B2

(12) United States Patent
Lund et al.

(10) Patent No.: US 9,827,102 B2
(45) Date of Patent: Nov. 28, 2017

(54) PENILE PROSTHESIS

(71) Applicant: AMS Research, LLC, Minnetonka, MN (US)

(72) Inventors: Jonathan J. Lund, Minnetonka, MN (US); Eric Forrest Little, Minnetonka, MN (US); Harshad M. Borgaonkar, Minnetonka, MN (US); Kristina Rouw, Minnetonka, MN (US); Andrew P. Vandeweghe, Minnetonka, MN (US); Carey J. Becker, Minnetonka, MN (US); Gregory J. Henkel, Minnetonka, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 374 days.

(21) Appl. No.: 14/362,048

(22) PCT Filed: Dec. 20, 2012

(86) PCT No.: PCT/US2012/070929
§ 371 (c)(1),
(2) Date: May 30, 2014

(87) PCT Pub. No.: WO2013/096615
PCT Pub. Date: Jun. 27, 2013

(65) Prior Publication Data
US 2014/0309490 A1 Oct. 16, 2014

Related U.S. Application Data

(60) Provisional application No. 61/578,509, filed on Dec. 21, 2011, provisional application No. 61/613,773, filed on Mar. 21, 2012.

(51) Int. Cl.
A61F 2/26 (2006.01)

(52) U.S. Cl.
CPC ........ A61F 2/26 (2013.01); A61F 2250/0003 (2013.01)

(58) Field of Classification Search
CPC ....................................... A61F 2/26
See application file for complete search history.

(56) References Cited

U.S. PATENT DOCUMENTS 5,067,485 A  11/1991  Cowen
5,112,295 A   5/1992  Zinner et al.
(Continued)

FOREIGN PATENT DOCUMENTS

WO  2010087769 A1  8/2010
WO  2013096615 A1  6/2013

OTHER PUBLICATIONS

EPO Communication from European Patent Application No. 12815935.7, dated Jul. 29, 2014.
(Continued)

Primary Examiner — Christine H Matthews
(74) Attorney, Agent, or Firm — Brake Hughes Bellermann LLP

(57) ABSTRACT

Embodiments are directed to an implantable penile prosthesis cylinder comprising an outer tube member and an inner tube member. The outer tube member has a longitudinal axis. The inner tube member is contained within the outer tube member. The inner tube member includes a plurality of inflatable chamber sections each defined by an exterior wall facing the outer tube member and an interior wall. Inflation of the chamber sections expands a girth of the outer tube member.

15 Claims, 6 Drawing Sheets

(56) References Cited

U.S. PATENT DOCUMENTS

| | | | | |
|---|---|---|---|---|
| 5,250,020 | A * | 10/1993 | Bley | A61F 2/26 600/40 |
| 2005/0014993 | A1* | 1/2005 | Mische | A61F 2/26 600/40 |
| 2009/0131745 | A1 | 5/2009 | George et al. | |
| 2010/0036196 | A1* | 2/2010 | Walch | A61F 2/26 600/40 |

OTHER PUBLICATIONS

International Search Report and Written Opinion of PCT/US2012/070929, dated Feb. 26, 2013.
First Examination Report for Australian Application No. 2012358834, dated Jan. 17, 2017, 3 pages.
Notice of Allowance for European Application No. 12815935.7, dated Nov. 9, 2016, 7 pages.

* cited by examiner

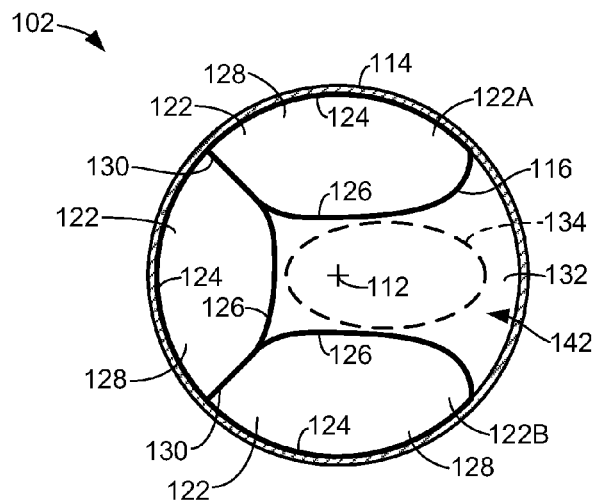
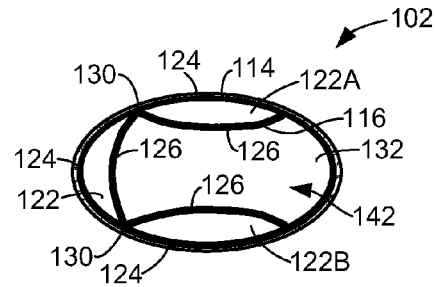
FIG. 2A
FIG. 2B
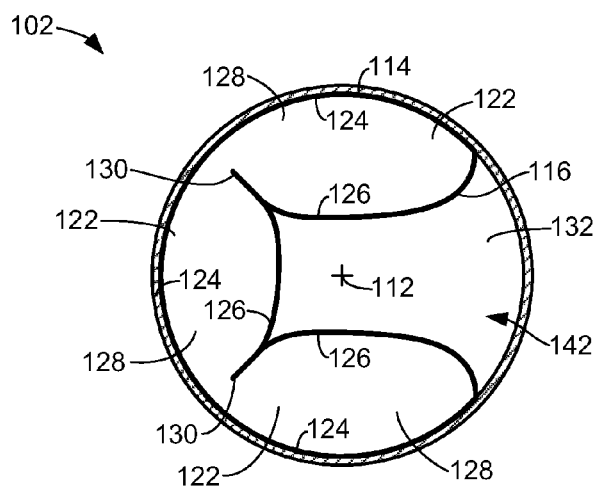
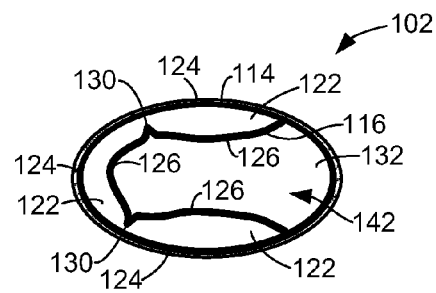
FIG. 3A
FIG. 3B

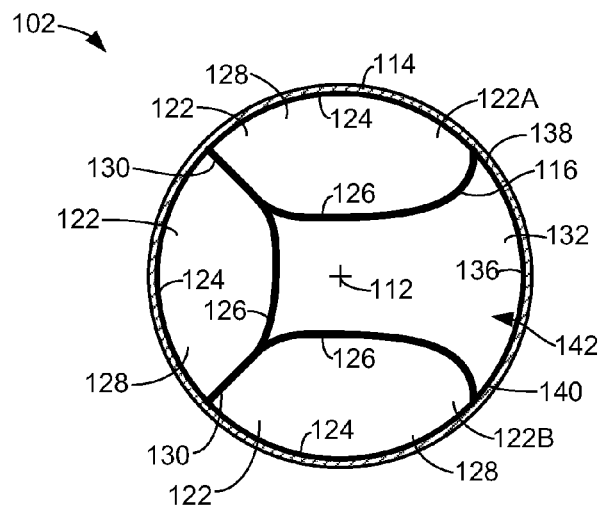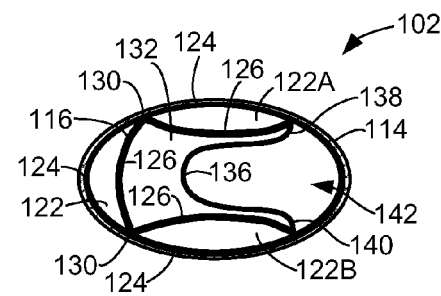
FIG. 4A
FIG. 4B
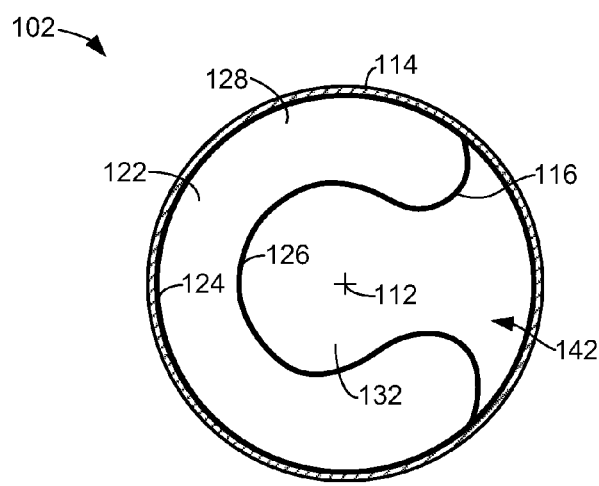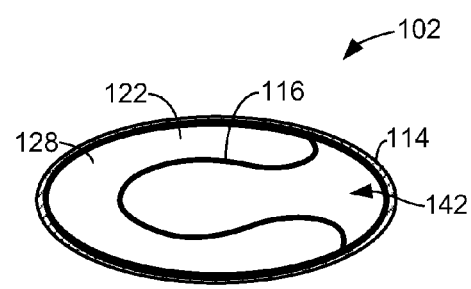
FIG. 5A
FIG. 5B

PENILE PROSTHESIS

CROSS-REFERENCE TO RELATED APPLICATION

This Application is a Section 371 National Stage Application of International Application No. PCT/US2012/070929, filed Dec. 20, 2012 and published as WO/2013/096615 A1 on Jun. 27, 2013, in English, which claims the benefit of U.S. Provisional Application Ser. No. 61/578,509, filed Dec. 21, 2011, and U.S. Provisional Application Ser. No. 61/613,773, filed Mar. 21, 2012 under 35 U.S.C. §119 (e). The contents of which are hereby incorporated by reference in their entirety.

FIELD OF THE INVENTION

The invention generally relates to penile prostheses and, more specifically, to penile prosthesis cylinders.

BACKGROUND OF THE INVENTION

Erectile dysfunction (ED) is the inability to get or keep an erection that is firm enough, or lasts long enough, to have successful sexual intercourse. It can have serious effects on a person's sexual relationship and their self-esteem. Erectile dysfunction is caused by several factors that contribute to erection and ejaculation. Physical and mental stimulants, hormones, neural transmissions and feedback, muscle contractions and relaxations, and cardiovascular blood flow all work together to create and maintain an erection leading to ejaculation. When any of these processes are disrupted, it can cause erectile dysfunction. The causes of ED are generally divided into two major categories: those that are psychological in nature and those that are physical (or organic) in nature.

When treating ED, there are many options to choose from, depending on the cause and nature of the problem. The treatments include: psychological, oral medications, vacuum pumps, transurethral therapy, injection therapy and surgical treatments. To treat a psychological cause, a doctor may recommend treatment from a qualified psychologist, psychiatrist, sex therapist or marriage counselor. Counseling can often resolve any psychological problems causing ED. Non-invasive treatments for ED include oral medications such as Viagra®, Cialis® and Levitra®. These medications improve blood flow to the penis by working directly on the blood vessels. They allow the arteries to expand, which could produce an erection. Pills are generally taken about an hour to several hours before planned sexual activity and must be combined with sexual stimulation to provide an erection. Vacuum pump therapy may be prescribed as a non-invasive treatment. When an erection is desired, the vacuum constriction device is placed over the penis. By withdrawing air, a vacuum is created, mechanically enhancing the flow of blood into the penis. A rubber ring placed around the base of the erect penis traps the blood inside the penis and maintains the erection. Transurethral therapy includes using an applicator, the patient inserts a small pellet of medication into the urethra opening at the end of the penis. The medication is absorbed into surrounding erectile tissue, causing blood vessels to relax so the penis fills with blood and becomes erect. Injection therapy uses a needle to inject medication directly into the base of the penis. The relaxation of muscle tissue allows blood to flow into the penis creating an erection. Finally, a penile implant, or a penile prosthesis, is concealed entirely within the body and requires some degree of manipulation before and after intercourse to make the penis erect or flaccid. There are different types of implants based on the manner of operation, naturalness of the erection and the number of components implanted.

A three-piece inflatable penile prosthesis provides a more natural appearing erection than the two-piece or malleable implants. A three-piece penile prosthesis typically consists of a pair of cylinders implanted in the corpus cavernosa, a single pump bulb implanted in the scrotum, and a reservoir implanted in the abdomen. This three-piece prosthesis acts and feels more like a natural erection compared to one-piece implants or two-piece implants. The three-piece prosthesis also expands the girth of the penis. Moreover, the three-piece feels softer and more flaccid when deflated compared to one-piece implants or two-piece implants. However, the three-piece prosthesis does have some challenges when in use such as the requirement of some manual dexterity, possibility of leakage, malfunction causing unintentional erections and implantation of a reservoir in the abdomen.

A two-piece inflatable prosthesis typically consists of a pair of cylinders implanted in the corpus cavernosum and a single pump bulb implanted in the scrotum. Patients simply squeeze the pump to inflate and bend the penis to deflate the prosthesis. This closed, fluid-filled system allows for good rigidity and partial flaccidity. Moreover, the two-piece penile prosthesis does not require an abdominal incision. However, the two-piece prosthesis does have some challenges when in use such as reduced flaccidity Both the three-piece and the two-piece penile inflatable prostheses rely on the transfer of a volume of fluid to and from the inflatable cylinders to transition the cylinders between inflated and deflated states. It is desirable to reduce this volume of fluid to reduce the amount of pumping required to be performed by the patient, and to reduce the size of the prosthesis.

SUMMARY OF THE INVENTION

Various embodiments described herein relate to an implantable penile prosthesis requiring a relatively low volume of fluid to transfer to and from the cylinders to transition the cylinders to erect and flaccid states.

Some embodiments of the invention are directed to an implantable inflatable penile prosthesis cylinder. In some embodiments, the inflatable penile prosthesis cylinder comprises an outer tube member having a longitudinal axis and an inner tube member contained within the outer tube member. In some embodiments, the inner tube member comprises a plurality of inflatable chamber sections each defined by an exterior wall facing the outer tube member and an interior wall. In some embodiments, inflation of the chamber sections expands a girth of the outer tube member and/or increases a stiffness of the outer tube member.

In some embodiments, the interior walls of adjoining chamber sections press against each other and the exterior walls press against the outer tube member when the chamber sections are inflated with fluid.

In some embodiments, the interior walls of adjoining chamber sections connect at a wall junction. In some embodiments, the wall junctions are attached to the exterior wall. In some embodiments, the inner tube member comprises at least two wall junctions. In some embodiments, each wall junction extends along a length of the inner tube member. In some embodiments, the wall junctions attach to the outer tube member.

In some embodiments, the inner tube member comprises an inner chamber formed between the interior walls of the chamber sections and the outer tube member. In some embodiments, a material is provided within the inner chamber. In some embodiments, the material comprises a fluid, an open-cell material, and/or a low-durometer silicone.

In some embodiments, the chamber sections are linked together at the wall junctions, such that the linked chamber sections include first and second end chamber sections. In some embodiments, the inner tube member comprises an outer wall member having a first end connected to the first end chamber section and a second end connected to the second end chamber section. In some embodiments, the inner chamber is formed between the interior walls of the chamber sections and the outer wall member.

In some embodiments, the interior walls of the chamber sections are thicker than the exterior walls.

In some embodiments, the penile prosthesis cylinder comprises an outer tube member, and a plurality of inflatable chamber sections within the outer tube member. In some embodiments, inflation of the chamber sections expands a girth of the outer tube member and/or increases a stiffness of the outer tube member.

In some embodiments, the chamber sections extend along a longitudinal axis of the cylinder and are dispersed around the longitudinal axis of the cylinder.

In some embodiments, the cylinder comprises a central chamber extending along the longitudinal axis. In some embodiments, the chamber sections are dispersed around an exterior of the central chamber. In some embodiments, the central chamber is configured to receive fluid from a fluid reservoir. In some embodiments, the central chamber is filled with an open-cell material or a low-durometer silicone.

In some embodiments, the chamber sections comprise ring-shaped chamber sections that are dispersed along a longitudinal axis of the cylinder.

In some embodiments, the chamber sections include a spiral-shaped chamber section that is substantially coaxial to a longitudinal axis of the cylinder.

Some embodiments of the invention are directed to a penile prosthesis comprising a pair of penile prosthesis cylinders formed in accordance with one or more embodiments described herein, and a pump configured to transfer fluid from a reservoir to the chamber sections of the cylinders.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The claimed subject matter is not limited to implementations that solve any or all disadvantages noted in the Background.

BRIEF DESCRIPTION OF THE DRAWINGS

FIGS. 2A and 2B are cross-sectional views of an exemplary inflatable penile prosthesis cylinder taken generally along line A-A of FIG. 1 respectively in inflated and deflated states in accordance with embodiments of the invention.

FIGS. 3A and 3B are cross-sectional views of an exemplary inflatable penile prosthesis cylinder taken generally along line A-A of FIG. 1 respectively in inflated and deflated states in accordance with embodiments of the invention.

FIGS. 4A and 4B are cross-sectional views of an exemplary inflatable penile prosthesis cylinder taken generally along line A-A of FIG. 1 respectively in inflated and deflated states in accordance with embodiments of the invention.

FIGS. 5A and 5B are cross-sectional views of an exemplary inflatable penile prosthesis cylinder taken generally along line A-A of FIG. 1 respectively in inflated and deflated states in accordance with embodiments of the invention.

DETAILED DESCRIPTION OF ILLUSTRATIVE EMBODIMENTS

Figure 1:
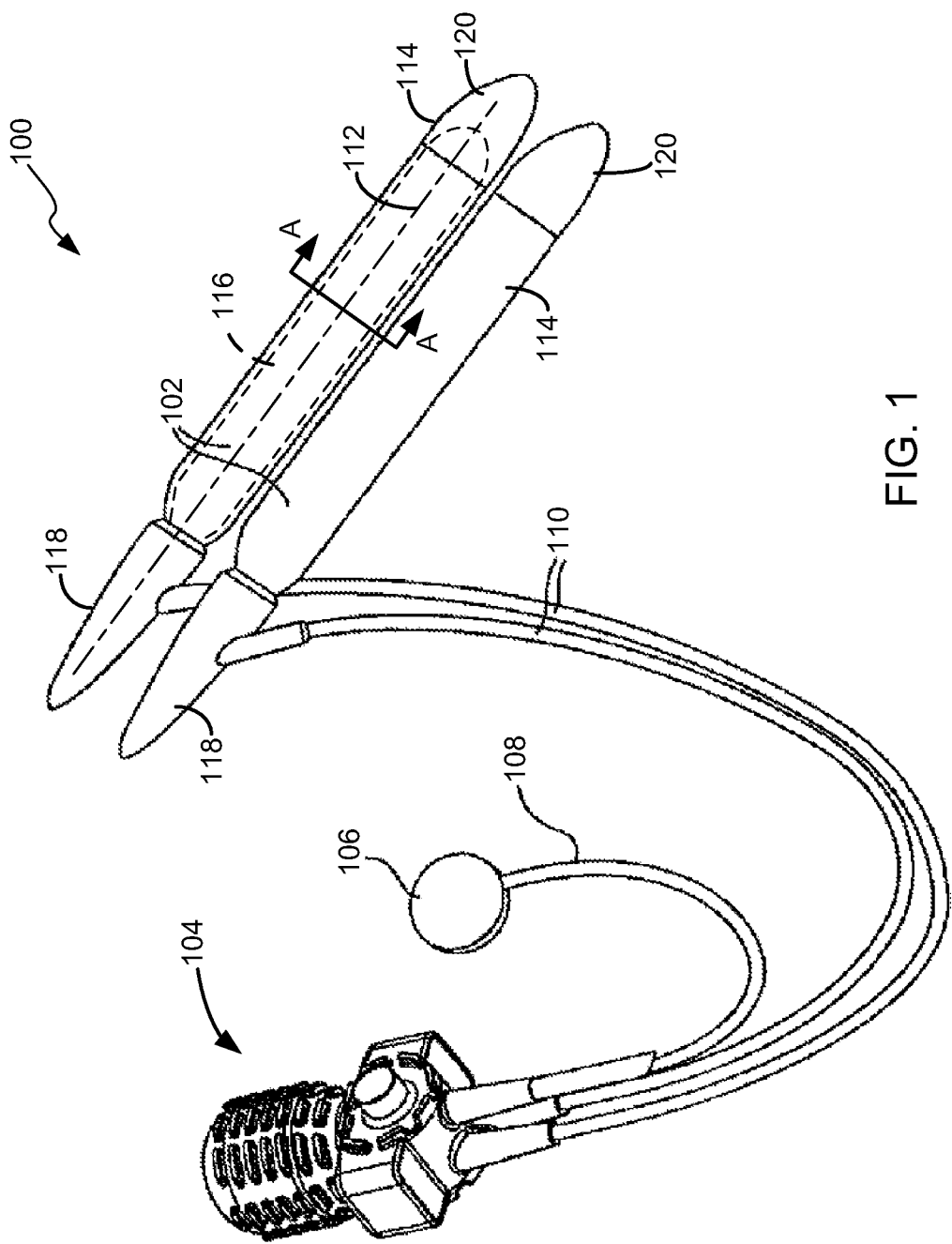
FIG. 1 is a schematic perspective view of an exemplary penile prosthesis comprising cylinders in accordance with one or more embodiments of the invention.
Figure 6A:
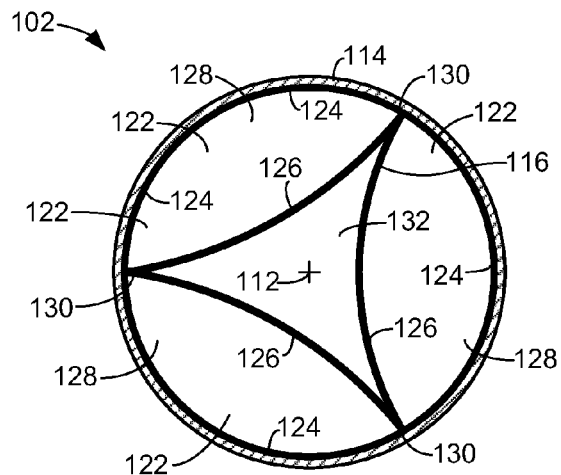
FIGS. 6A and 6B are cross-sectional views of an exemplary inflatable penile prosthesis cylinder taken generally along line A-A of FIG. 1 respectively in inflated and deflated states in accordance with embodiments of the invention.
Figure 6B:
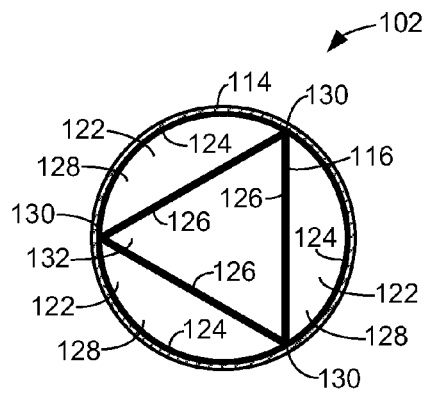
Figure 7A:
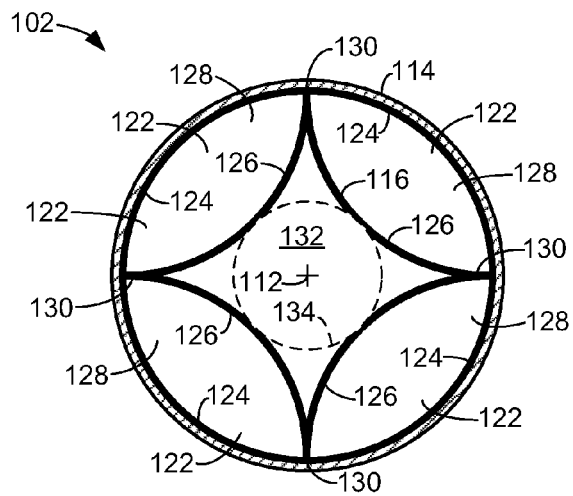
FIGS. 7A and 7B are cross-sectional views of an exemplary inflatable penile prosthesis cylinder taken generally along line A-A of FIG. 1 respectively in inflated and deflated states in accordance with embodiments of the invention.
Figure 7B:
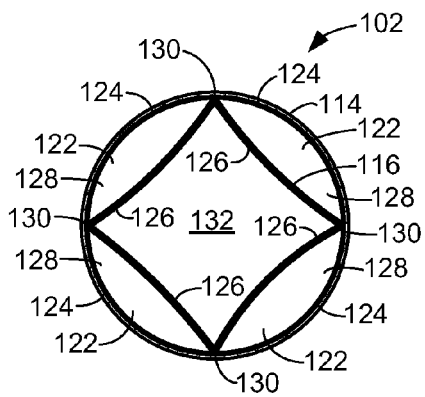

Embodiments of the invention are described more fully hereinafter with reference to the accompanying drawings. The various embodiments of the invention may, however, be embodied in many different forms and should not be construed as limited to the embodiments set forth herein. Rather, these embodiments are provided so that this disclosure will be thorough and complete, and will fully convey the scope of the invention to those skilled in the art. Elements that are identified using the same or similar reference characters refer to the same or similar elements.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

It will be understood that when an element is referred to as being "connected" or "coupled" to another element, it can be directly connected or coupled to the other element or intervening elements may be present, and both of these options are covered by the term. In contrast, if an element is referred to as being "directly connected" or "directly coupled" to another element, there are no intervening elements present.

It will be understood that, although the terms first, second, etc. may be used herein to describe various elements, these elements should not be limited by these terms. These terms are only used to distinguish one element from another. Thus, a first element could be termed a second element without departing from the teachings of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

FIG. 1 is a schematic perspective view of an exemplary penile prosthesis 100 comprising cylinders 102 formed in accordance with one or more embodiments described herein. In some embodiments, the cylinders 102 have a unique inner tube geometry that allows for inflation of the cylinders 102 using less fluid than conventional penile prosthesis cylinders. While the exemplary penile prosthesis 100 is depicted as a three-piece inflatable penile prosthesis, the cylinders 102 may also be used with two-piece inflatable penile prostheses or other penile prostheses that utilize inflatable cylinders, as is readily apparent to those skilled in the relevant art.

In some embodiments, the penile prosthesis 100 includes a pump 104, a reservoir 106, tubing 108 fluidically coupling the reservoir 106 to the pump 104, and tubing 110 fluidically coupling the pump 104 to the cylinders 102. Fluid is pumped from the reservoir 106 through the tubing 108 and the tubing 110 to each of the cylinders 102 using the pump 104 to inflate the cylinders 102 to place them in an inflated or rigid state corresponding to an erect penis condition. The cylinders 102 may then be deflated using conventional techniques that transfer fluid from the cylinders 102 back to the reservoir 106 through the tubing 110 and 108.

In some embodiments, each penile prosthesis cylinder 102 has a longitudinal axis 112 oriented along the length of the cylinder 102, as shown in FIG. 1. In some embodiments, each cylinder 102 includes an outer tube member 114 and an inner tube member 116 contained within the outer tube member 114. The outer tube member 114 has a longitudinal axis that is approximately coaxial to the longitudinal axis 112 of the cylinder 102.

The cylinders 102 may also comprise conventional components, such as a rear tip 118, an end cap 120 and fluid conduit fluidically connecting the tubing 110 to one or more inflatable chambers contained within the outer tube member 114. The rear tip 118 and the end cap 120 can be used to seal the cylinder 102 and form a closed system, once implanted, in relation to the external environment of the corpus cavernosum. The cylinders 102 may also comprise conventional components that are not shown in the drawings in order to simplify the illustrations.

In some embodiments, the cylinders 102 are formed using conventional penile prosthesis cylinder materials that are medically safe and provide a necessary degree of structural reliability. For instance, the outer tube member 114 and the inner tube member 116 may be formed of silicone or polyurethane. Components of the cylinders 102 may also comprise synthetic materials such as various types of rubbers, neoprene, nylon, PVC, polystyrene, polyethylene, polypropylene and bio compatible polymers known to those skilled in the art.

In some embodiments, the outer tube member 114 is the portion of the penile prosthesis cylinder 102 that is in direct contact with the lumen of the corpus cavernosum when implanted. However, it is understood that a sheath or other component may be inserted between the outer tube member 114 and the corpus cavernosum. In some embodiments, the outer tube member 114 provides an enclosure for the inner tube member 116, as well as conventional components, such as an internal reservoir, fluid flow paths or block, and other components.

In some embodiments, the inner tube member 116 comprises a plurality of inflatable chamber sections 122 that are fluidically coupled to a source of fluid, such as the reservoir 106. The chambers are inflated by receiving a volume of the fluid, such as through the actuation of the pump 104. In some embodiments, this inflation of the chamber sections 122 causes the girth or diameter of the outer tube member 114 to expand and/or stiffen, and places cylinder 102 in the inflated state.

In some embodiments, the chamber sections 122 of the inner tube member 116 allow for a reduced volume of fluid to be used to transition the cylinder 102 from a deflated state, corresponding to a flaccid penis state, to the inflated state, as compared to conventional penile prosthesis cylinders. As a result, the penile prosthesis 100 can operate utilizing a smaller volume fluid source, such as a smaller reservoir 106, than conventional penile prostheses. Additionally, transitioning the penile prosthesis from a deflated state to an inflated state may be accomplished by the patient with less effort due to the lower volume of fluid that must be transferred to the cylinders 102.

FIGS. 2-7 are simplified cross-sectional views of the exemplary cylinder 102 of FIG. 1 taken generally along line A-A in accordance with embodiments of the invention. As mentioned above, one embodiment of the inner tube member 116 comprises a plurality of inflatable chamber sections 122 that are contained within the outer tube member 114. In some embodiments, the inner tube member 116 includes at least three chamber sections 122 and two wall junctions 130, as illustrated in FIGS. 2-4, 6 and 7. In some embodiments, the inflated cross-sectional shape of the inner tube member 116 is dissimilar to the cross-sectional shape of the outer tube member 114.

In some embodiments, the inner tube member 116 is a separate structure in relation to the outer tube member 114. In some embodiments, walls of the inner tube member 116 completely define the chamber sections 122, as shown in FIGS. 2-7. That is, each of the chamber sections 122 includes an exterior wall 124 and an interior wall 126, which enclose an interior cavity 128 of the chamber section 122, in at least a plane extending perpendicular to the longitudinal axis 112, as shown in FIG. 2A.

In some embodiments, the inner tube member 116, or portions thereof, are allowed to slide relative to the outer tube member 114. A coating, such as Parylene™ may be applied to the inner surface of the outer tube member 114 and/or to the outer surface of the exterior walls 124 of the inner tube member, to provide a slippery, wear-resistant interface between the inner tube member 116 and the outer tube member 114.

In some embodiments, the chamber sections 122 of the inner tube member 116 may be defined by the interior walls 126 and the outer tube member 114. That is, the exterior walls 124 of the inner tube member 116 illustrated in FIG. 2A are replaced by the adjoining wall of the outer tube member 114. The interior walls 126 form a seal against the inner tube member 114 to form the inflatable chambers 122.

In some embodiments, inflation of the chamber sections 122 through the pumping of fluid into the interior cavities 128, causes the chamber sections 122 to inflate, as illustrated in FIGS. 2A, 3A, 4A, 5A, 6A and 7A. In some embodiments, the inflation of the chamber sections 122 expand a girth or radial diameter of the outer tube member 114 to place the cylinder 102 in the inflated state. In some embodiments, the inflation of the chamber sections 122 causes the exterior walls 124 of the chamber sections 122, which face the outer tube member 114, to press against the outer tube member 114 and expand the outer tube member 114 radially relative to the longitudinal axis 112. In some embodiments, the interior walls 126 of the chamber sections 122 are thicker than the exterior walls 124. This encourages the chamber sections 122 to inflate outward toward the outer tube member 114.

In some embodiments, the contact between the chamber sections 122 of the inner tube member 116 and the outer tube member 114 may be mechanical, chemical or both. Thus, the inner tube member 116, when inflated, may be disposed upon the inner surface of the outer tube member 114 to cause the outer tube member 114 to become rigid when the chamber sections 122 are inflated. The inner tube member 116 may also be chemically coupled to the inner surface of the outer tube member 114 at various contact points, which remain attached to the outer tube member 114 during inflated and deflated states of the cylinder 102.

In some embodiments, portions of the interior walls 126 of adjoining chamber sections 122 press against each other during inflation, as shown in FIGS. 2A, 3A, 4A, 6A and 7A. This causes the exterior walls 124 of the chamber sections 122 to press against the inner surface of the outer tube member 114 and causes the outer tube member 114 to expand radially and/or stiffen to place the cylinder 102 in the inflated state.

As the chamber sections 122 are deflated through the removal of fluid from the interior cavities 128 using conventional techniques, the cylinder 102 transitions to the deflated state, as illustrated in FIGS. 2B, 3B, 4B, 5B, 6B and 7B. This deflation of the chamber sections 122 causes a reduction in the pressure exerted by the exterior walls 124 on the inner surface of the outer tube member 114, allowing the outer tube member 114 to contract radially. In some embodiments, the radial contraction of the cylinder 102 also results in a reduction in the rigidity of the cylinder 102.

In some embodiments, the interior walls 126 of adjoining chamber sections 122 are connected at a wall joint junction 130. In some embodiments, the wall junctions 130 define fold lines or creases in the inner tube section 116, at which the interior walls 126 overlap and engage each other as the chamber sections 122 are inflated, as shown in FIGS. 2A, 3A, 4A, 6A and 7A. In some embodiments, the wall junctions 130 extend in continuous lines in the direction of the longitudinal axis 112 along the length of the inner tube member 116. In other embodiments, portions of the interior walls 126 of adjoining chamber sections 122 are connected to each other to form the creases in the inner tube member 116 and define the fold lines where the interior walls 126 of adjoining chamber sections 122 overlap upon inflation of the chamber sections 122.

In some embodiments, the wall junctions 130 are connected to the exterior wall 124 of the inner tube member 116, as shown in FIGS. 2, 4, 6 and 7. In other embodiments, when the exterior wall 124 of the inner tube member is replaced by the outer tube member 114, the wall junctions 130 are connected to the outer tube member 114.

In some embodiments, the wall junctions 130 are not attached to the exterior wall 124 of the inner tube member or the outer tube member 114, as illustrated in FIGS. 3A and 3B. Thus, the chamber sections 122 may not be completely sealed from each other, but are distinguished from each other by the wall junction 130 and the fold or crease in the interior walls 126.

In some embodiments, an inner chamber 132 is formed between the interior walls 126 of the chamber sections 122 when the chamber sections 122 are inflated, as shown in FIGS. 2A, 3A, 4A, 6A and 7A. In some embodiments, the inner chamber 132 is completely or partially devoid of fluid. As a result, the inflated state of the cylinder 102 is attained through the inflation of the chamber sections 122, which do not fill the entire cross-sectional area within the outer tube member 114 due to the inner chamber 132. Accordingly, the cylinder 102 may be placed in the inflated state without having to completely fill the interior volume of the outer tube member 114 with fluid. Instead, a reduced volume of fluid may be used to inflate the chamber sections 122 in order to generate the desired radial pressure on the inner surface of the outer tube member 114 to place the cylinder 102 in the inflated state.

In some embodiments, the cylinder 102 may comprise an object or material, represented by 134, within the inner chamber 132. In one embodiment, the inner chamber 132 contains the material 134 comprising fluid, which allows the inner chamber 132 to operate as a reservoir. The fluid 134 within the inner chamber 132 may be contained within its own collapsible container, or be contained within the walls of the inner chamber 132. The fluid 134 may replace or supplement fluid contained in conventional reservoirs, such as reservoir 106 (FIG. 1). In some embodiments, the actuation of the pump 104 drives the fluid 134 from the inner chamber 132 into the chamber sections 122 to transition the cylinder from a deflated state to the inflated state.

In some embodiments, the object or material 134 contained within the inner chamber 132 comprises an open-cell material, or a low-durometer silicone. In accordance with this embodiment, the object or material 134 fills at least a portion of the volume of the inner chamber 132 and provides a structure against which the interior walls 126 of the chamber sections 122 can press as the chamber sections 122 are inflated to increase the radial pressure exerted against the outer tube member 114 by the exterior walls 124. One potential advantage of this embodiment is the ability to provide a desired radial expansion or increased stiffness of the outer tube member 114 while potentially using even less fluid than would be possible when such material 134 is not provided in the inner chamber 132.

In some embodiments, the chamber sections 122 are linked together at the wall junctions 130, as shown, for example, in FIGS. 2A, 3A and 4A. As a result, the linked chamber sections 122 include end chamber sections 122A and 122B. In one embodiment, the inner tube member 116 comprises an outer wall member 136 having an end 138 connected to the end chamber section 122A and an end 140 connected to the end chamber section 122B, as shown in FIGS. 4A and 4B. In one embodiment, the inner chamber 132 is defined by the interior walls 126 of the chamber sections 122 and the outer wall member 136. In some embodiments, the outer wall member 136 is configured to fold between the chamber sections 122 as the chamber sections 122 are deflated, as illustrated in FIG. 4B. As a result, the outer wall member 136 may accommodate a vacuum formed within the inner chamber 132 as the cylinder 102 transitions from the inflated state to the deflated state. This may be desirable when a fluid within the inner chamber 132 is pumped out of the inner chamber 132 to inflate the chamber sections 122.

In the embodiment of the cylinder 102 illustrated in FIGS. 5A and 5B, the interior tube member 116 comprises a single chamber section 122, which is formed in the shape of a ring, or a partial ring (C-shaped). In some embodiments, the single chamber section 122 has a quiescent or unconstrained state that is substantially planer. The single chamber section 122 is bent when it is installed within the outer tube member 114. As the single chamber section 122 is inflated within the outer tube member 114, the ends 122A and 122B press against the inner surface of the outer tube member 114 to produce the desired radial expansion of the outer tube member 114.

In some embodiments, the inner tube member 116 comprises an open side 142 where a gap exists between the ends 122A and 122B of the inner tube member 116, as shown in FIGS. 2-5. In some embodiments, the open side 142 allows the inner tube member 116 to flatten as the chamber sections 122 are deflated, as shown in FIGS. 2B, 3B, 4B and 5B. In some embodiments, the cylinder 102 is implanted in the corpus cavernosum of a patient such that the open side 142 faces the longitudinal/axial midline septum between the penile corpora a second mirror imaged cross-sectional cylinder in the adjacent corpora also facing the longitudinal midline. The flattening of the deflated cylinder 102 when implanted in this manner, feels more natural upon palpitation.

In accordance with some embodiments, the chamber sections 122 extend substantially around the entire inner wall of the outer tube member 114 resulting in little or no open side 142, as illustrated in FIGS. 6 and 7. As discussed above, the interior walls 124 of the chamber sections 122 press against each other proximate at least the wall junctions 130 and radial pressure is applied to the outer tube member 114 by the exterior walls 124. In some embodiments, a material or object 134 may be located within the inner chamber 132, as described above.

Figure 8:
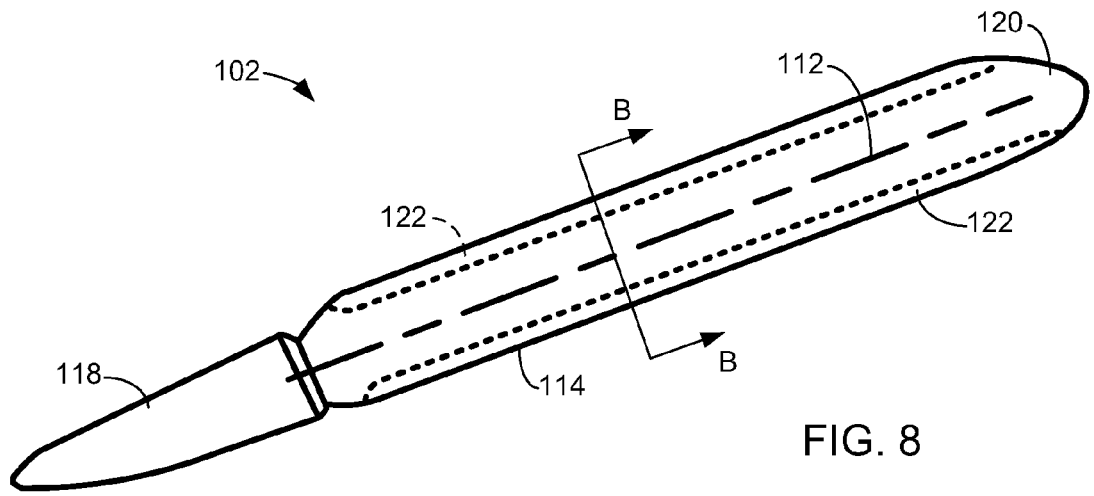
FIG. 8 is a side view of an exemplary inflatable penile prosthesis cylinder in accordance with embodiments of the invention in accordance with embodiments of the invention.

As mentioned above, the chamber sections 122 of the penile prosthesis cylinder 102 may extend along the longitudinal axis 112 of the cylinder 102, as illustrated in the side view of an exemplary cylinder 102 provided in FIG. 8. Each of the chamber sections 122 are contained within the outer tube member 114 and operate to expand a girth or radial diameter of the outer tube member 114 and/or increase a stiffness of the outer tube member 114.

Figure 9:
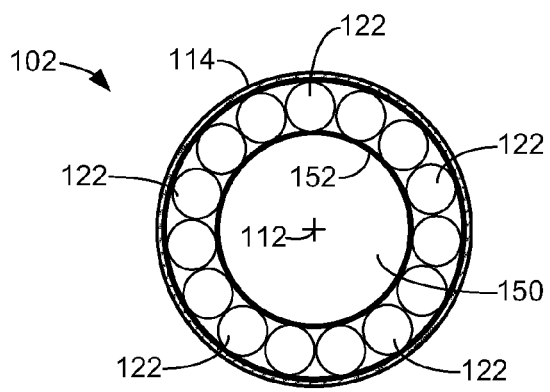
FIGS. 9 and 10 are simplified side cross-sectional views of the penile prosthesis cylinder of FIG. 8 taken generally along line B-B in accordance with embodiments of the invention.
Figure 10:
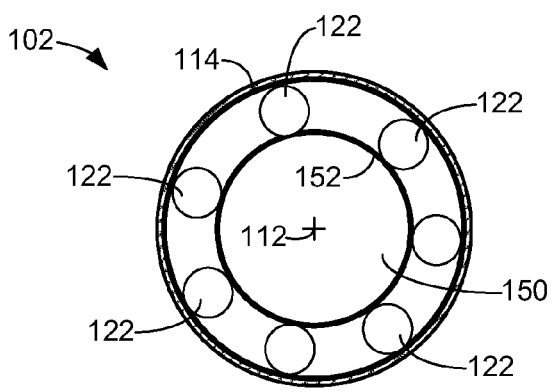

FIGS. 9 and 10 are cross-sectional views of the exemplary penile prosthesis cylinder 102 of FIG. 8 taken generally along line B-B in accordance with embodiments of the invention. In some embodiments, the chamber sections 122 are dispersed around the longitudinal axis 112 of the cylinder 102.

In some embodiments, the cylinder 102 comprises a central chamber 150 that extends along the longitudinal axis 112. In some embodiments, the inflatable chamber sections 122 are dispersed around an exterior 152 of the central chamber 150, as shown in FIGS. 9 and 10. In some embodiments, the central chamber 150 is filled with an open cell material or a low durometer silicone. In some embodiments, the central chamber 150 includes embodiments similar to those discussed above with regard to chamber 132. For instance, the central chamber 150 may contain the object or material 134 discussed above, such as a fluid, an open-cell material, or a low-durometer silicone. This material within the central chamber 150 provides a structure against which the inflatable chamber sections 122 can press when inflated to increase the stiffness of the cylinder 102 and/or increase the girth or radial diameter of the cylinder 102 when in the inflated state.

In some embodiments, the inflatable chamber sections 122 are configured to engage adjoining chamber sections 122 when inflated, as illustrated in FIG. 9. In accordance with other embodiments, the inflatable chamber sections 122 are dispersed around the central chamber 150 such that they do not engage adjoining chamber sections 122, as shown in FIG. 10. In some embodiments, the chamber sections 122 are fluidically interconnected such that the chamber sections 122 fill with fluid simultaneously when fluid is fed from a reservoir using the pump 104.

Figure 11:
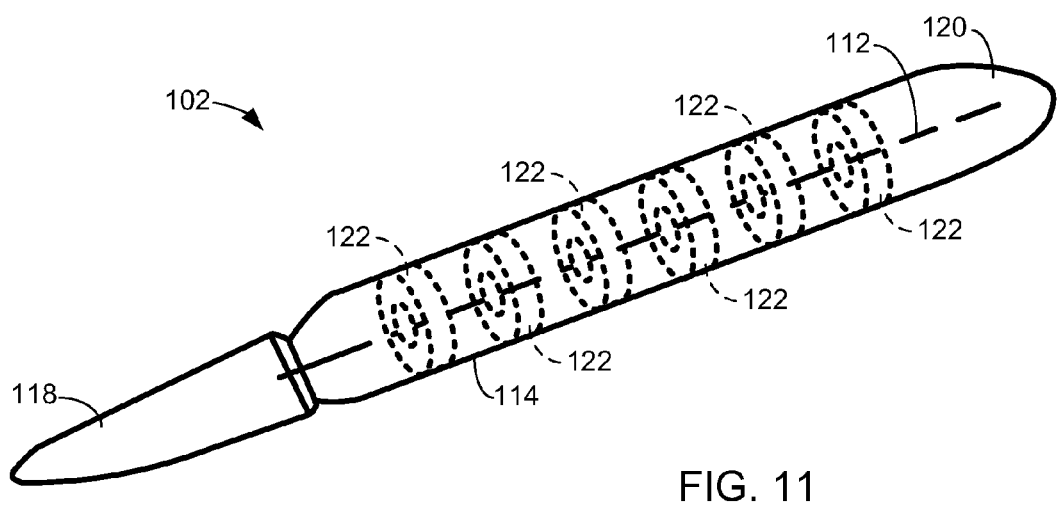
FIGS. 11 and 12 are simplified side views of exemplary inflatable penile prosthesis cylinders in accordance with embodiments of the invention.

In some embodiments, the inflatable chamber sections 122 include one or more ring-shaped chamber sections 122 dispersed along the longitudinal axis 112 of the cylinder 102, as shown in the side view of an exemplary penile prosthesis cylinder provided in FIG. 11. When the ring-shaped chamber sections 122 are inflated and pressurized with a fluid, they each form a circumferential "rib" that resists kinking or flattening of the cylinder 102. The ring-shaped chamber sections 122 may also increase the girth or radial diameter of the cylinder 102 when inflated.

Figure 12:
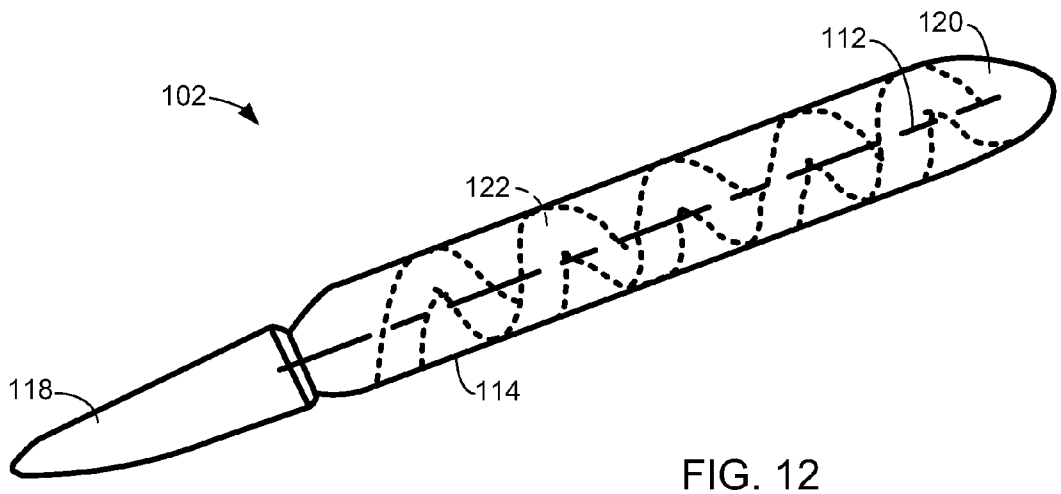

In accordance with another embodiment, the penile prosthesis cylinder 102 may comprise a spiral-shaped chamber section 122 that is substantially coaxial to the longitudinal axis 112, as shown in FIG. 12. Inflation of the spiral-shaped chamber section 122 applies a radial pressure to the outer tube member 114 which stiffens and/or increases the radial diameter of the outer tube member 114. The increase in rigidity to the cylinder 102 responsive to the inflation of the spiral-shaped chamber section 122 resists kinking or flattening of the cylinder 102.

In accordance with some embodiments, one or more of the chamber sections 122 described above, comprises a reinforcement filament, which biases the chamber section 122 in at least a partially inflated condition even when the other chamber sections 122 are drained of fill fluid. In some embodiments, these chamber sections are not configured to receive the fill fluid.

In some embodiments, one or more of the chamber sections 122 are filled with an open-cell material. The open-cell material allows the fill fluid to fill the entirety of the chamber sections 122 while further reducing the overall amount of fluid required to fill and pressurize the chamber sections 122.

In some embodiments, the inner chamber 132 (FIGS. 2-7) and the central chamber 150 (FIGS. 9 and 10) can be passively linked to the pump 104 or the reservoir 106. In this configuration, when the chamber sections 122 are filled with the fill fluid to expand the chamber sections 122 and the cylinder 102, a quantity of the fill fluid can be passively drawn from the pump 104 or the reservoir 106 into the inner chamber 132 or the central chamber 150. One advantage of this configuration is that inflating the inflatable chamber sections 122 does not create a vacuum within the inner chamber 132 or the central chamber 150, which could make inflation of the cylinder 102 more difficult.

In accordance with some embodiments, the pump 104 can be configured to provide a smaller volume of fluid to the chamber sections 122 at a higher pressure than conventional pumps. This configuration compensates for the reduced amount of fill fluid required to inflate the chamber sections 122, and the increased difficulty required to pressurize the smaller diameter chamber sections 122.

Some embodiments are directed to a method of operating the penile prosthesis 100 formed in accordance with one or more of the embodiments described above. In one embodiment, the pump 104 is actuated to draw a quantity of fluid from the reservoir 106 and drive the fluid into each of the chamber sections 122. The chamber sections 122 expand and become rigid in response to the reception of the fluid. In some embodiments, this inflation of the chamber sections 122 produces a radial force against the outer tube member 114, which radially expands the outer tube member 114 and/or stiffens the outer tube member 114 to place the cylinder 102 in the inflated state. In some embodiments, the cylinder 102 is returned to the deflated state by venting the inflatable chambers 122 of the fill fluid by allowing the fill fluid to return to the reservoir 106.

Although the present invention has been described with reference to preferred embodiments, workers skilled in the art will recognize that changes may be made in form and detail without departing from the spirit and scope of the invention.

What is claimed is:

1. An implantable penile prosthesis comprising:
a pair of penile prosthesis cylinders, each of the pair of penile prosthesis cylinders including:
an outer tube member; and
an inner tube member included within the outer tube member, the inner tube member including a plurality of inflatable chamber sections each defined by an exterior wall and an interior wall that enclose an interior cavity of a respective chamber section, at least a portion of the exterior walls contacting the outer tube member, the inner tube member including an inner chamber defined at least partially by the interior walls of the chamber sections, the inner chamber being separate from the chamber sections, the inner chamber extending along a longitudinal axis of a respective cylinder, the chamber sections being disposed adjacent to the inner chamber,
wherein the chamber sections are configured to receive inflation fluid during an inflation state such that inflation of the chamber sections expands a girth of the outer tube member.

2. The penile prosthesis in accordance with claim 1, wherein the interior walls of adjoining chamber sections press against each other and the exterior walls press against the outer tube member when the chamber sections are inflated with the inflation fluid.

3. The penile prosthesis in accordance with claim 1, further comprising wall junctions at which portions of the interior walls of adjoining chamber sections are connected.

4. The penile prosthesis in accordance with claim 3, wherein the wall junctions are attached to the exterior walls.

5. The penile prosthesis in accordance with claim 1, wherein the inner chamber is devoid of inflation fluid when transitioning from a deflation state to the inflation state.

6. The penile prosthesis in accordance with claim 3, wherein each of the wall junctions extends along a length of the inner tube member.

7. The penile prosthesis in accordance with claim 1, wherein the inner chamber is defined by the interior walls of the chamber sections and the outer tube member.

8. The penile prosthesis in accordance with claim 3, wherein:
the chamber sections are linked together at the wall junctions, the linked chamber sections including a first chamber section and a second chamber section;
the inner tube member comprises an outer wall member having a first end connected to the first chamber section and a second end connected to the second chamber section; and
the inner chamber is formed between the interior walls of the chamber sections and the outer wall member.

9. The penile prosthesis in accordance with claim 1, wherein the inner chamber includes a material, the material including a silicone-based material.

10. The penile prosthesis in accordance with claim 1, wherein the interior walls of the chamber sections are thicker than the exterior walls of the chamber sections.

11. The penile prosthesis in accordance with claim 1 comprising:
a pump configured to transfer the inflation fluid from a reservoir to the chamber sections of the pair of penile prosthesis cylinders.

12. An implantable penile prosthesis comprising:
a pair of penile prosthesis cylinders, each of the pair of penile prosthesis cylinders including:
an outer tube member; and
an inner tube member disposed within the outer tube member, the inner tube member including a plurality of inflatable chamber sections, each chamber section being defined by an exterior wall and an interior wall that enclose an interior cavity of a respective chamber section, at least a portion of the exterior walls contacting the outer tube member, the inner tube member including an inner chamber defined at least partially by the interior walls of the chamber sections, the inner chamber being separate from the chamber sections, the inner chamber extending along a longitudinal axis of a respective cylinder, the chamber sections being disposed adjacent to the inner chamber;
wherein the chamber sections are configured to receive inflation fluid during an inflation state such that inflation of the chamber sections expands a girth of the outer tube member and increases a stiffness of the outer tube member, the inner chamber being devoid of inflation fluid during the inflation state.

13. The penile prosthesis in accordance with claim 12, wherein the chamber sections are disposed outside an exterior of the inner chamber.

14. The penile prosthesis in accordance with claim 12, wherein the inner chamber includes an open-cell material.

15. The penile prosthesis of claim 12, further comprising:
a pump configured to transfer the inflation fluid from a reservoir to the chamber sections of the pair of penile prosthesis cylinders.

* * * * *